United States Patent
May et al.

(10) Patent No.: US 8,562,608 B2
(45) Date of Patent: Oct. 22, 2013

(54) PATELLO-FEMORAL MILLING SYSTEM

(75) Inventors: Justin J. May, Leesburg, IN (US); Jason F. Detweiler, Warsaw, IN (US); Raymond C. Parisi, Wakarusa, IN (US); Adam M. Griner, Columbia City, IN (US); Toby N. Farling, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 908 days.

(21) Appl. No.: 12/562,168

(22) Filed: Sep. 18, 2009

(65) Prior Publication Data

US 2010/0076441 A1 Mar. 25, 2010

Related U.S. Application Data

(60) Provisional application No. 61/098,352, filed on Sep. 19, 2008.

(51) Int. Cl.
| | |
|---|---|
| A61B 17/00 | (2006.01) |
| A61B 17/58 | (2006.01) |
| A61B 17/60 | (2006.01) |
| A61F 5/00 | (2006.01) |
| A61F 2/00 | (2006.01) |

(52) U.S. Cl.
USPC .................... 606/79; 606/87; 606/88

(58) Field of Classification Search
USPC .............................. 606/79, 87, 88
See application file for complete search history.

(56) References Cited

U.S. PATENT DOCUMENTS

| | | |
|---|---|---|
| 3,748,662 A | 7/1973 | Helfet |
| 4,719,908 A | 1/1988 | Averill et al. |
| 4,964,868 A | 10/1990 | Bloebaum |
| 5,035,699 A | 7/1991 | Coates |
| 5,037,439 A | 8/1991 | Albrektsson et al. |
| 5,100,409 A | 3/1992 | Coates et al. |
| 5,176,684 A | 1/1993 | Ferrante et al. |
| 5,312,408 A | 5/1994 | Brown |
| 5,334,205 A | 8/1994 | Cain |
| 5,344,423 A | 9/1994 | Dietz et al. |
| 5,346,496 A | 9/1994 | Pennig |
| D357,315 S | 4/1995 | Dietz |
| 5,413,606 A | 5/1995 | Fisk et al. |

(Continued)

FOREIGN PATENT DOCUMENTS

| | | |
|---|---|---|
| EP | 0554959 A1 | 8/1993 |
| EP | 0647432 A1 | 4/1995 |

(Continued)

OTHER PUBLICATIONS

Partial Search Report from EP06736184.0—published as EP1887951A1.

Primary Examiner — Nicholas Woodall
Assistant Examiner — Christine Nelson
(74) Attorney, Agent, or Firm — Schwegman, Lundberg & Woessner, P.A.

(57) ABSTRACT

An orthopedic system prepares a surface of an anatomical structure to receive an orthopedic prosthesis. A method for using the same is also disclosed. The orthopedic system includes a surgical instrument and a guide. The guide includes an anterior portion and a distal portion that is at least partially elevated relative to the anterior portion. The distal portion includes at least one track that is sized to receive the surgical instrument while preparing the surface of the anatomical structure.

12 Claims, 12 Drawing Sheets

(56) References Cited

U.S. PATENT DOCUMENTS

| | | |
|---|---|---|
| 5,417,695 A | 5/1995 | Axelson, Jr. |
| 5,474,559 A | 12/1995 | Bertin et al. |
| 5,484,446 A | 1/1996 | Burke et al. |
| 5,486,180 A | 1/1996 | Dietz et al. |
| D376,202 S | 12/1996 | Burke et al. |
| 5,593,411 A | 1/1997 | Stalcup et al. |
| 5,609,642 A | 3/1997 | Johnson et al. |
| 5,634,927 A | 6/1997 | Houston et al. |
| 5,653,714 A | 8/1997 | Dietz et al. |
| 5,709,689 A | 1/1998 | Ferrante et al. |
| 5,743,915 A | 4/1998 | Bertin et al. |
| 5,755,803 A | 5/1998 | Haines et al. |
| 5,769,855 A | 6/1998 | Bertin et al. |
| 5,860,981 A | 1/1999 | Bertin et al. |
| 5,885,035 A | 3/1999 | Hoffschneider |
| 5,908,424 A | 6/1999 | Bertin et al. |
| 6,063,091 A | 5/2000 | Lombardo et al. |
| 6,132,468 A | 10/2000 | Mansmann |
| 6,159,216 A | 12/2000 | Burkinshaw et al. |
| 6,355,045 B1 | 3/2002 | Gundlapalli et al. |
| 6,436,101 B1 | 8/2002 | Hamada |
| 6,482,209 B1 | 11/2002 | Engh et al. |
| 6,554,838 B2 | 4/2003 | McGovern et al. |
| 6,620,168 B1 | 9/2003 | Lombardo et al. |
| 6,712,824 B2 | 3/2004 | Millard et al. |
| 6,969,393 B2 | 11/2005 | Pinczewski et al. |
| 7,727,239 B2 | 6/2010 | Justin et al. |
| 7,794,462 B2 | 9/2010 | May et al. |
| 2002/0019637 A1 | 2/2002 | Frey et al. |
| 2002/0198528 A1 | 12/2002 | Engh et al. |
| 2003/0028196 A1 | 2/2003 | Bonutti |
| 2003/0130665 A1 | 7/2003 | Pinczewski et al. |
| 2004/0220583 A1 | 11/2004 | Pieczynski, II et al. |
| 2005/0015153 A1 | 1/2005 | Goble et al. |
| 2005/0049603 A1* | 3/2005 | Calton et al. .................... 606/87 |
| 2005/0143745 A1 | 6/2005 | Hodorek et al. |
| 2005/0143831 A1 | 6/2005 | Justin et al. |
| 2005/0192588 A1 | 9/2005 | Garcia |
| 2006/0004374 A1 | 1/2006 | Griner et al. |
| 2006/0009776 A1 | 1/2006 | Justin |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0058803 A1* | 3/2006 | Cuckler et al. .................... 606/79 |
| 2006/0167460 A1 | 7/2006 | Pinczewski et al. |
| 2006/0184176 A1 | 8/2006 | Straszheim-Morley et al. |
| 2006/0200158 A1 | 9/2006 | Farling et al. |
| 2006/0200161 A1 | 9/2006 | Plaskos et al. |
| 2006/0217734 A1 | 9/2006 | Sanford et al. |
| 2006/0276796 A1 | 12/2006 | Creger et al. |
| 2006/0293681 A1 | 12/2006 | Claypool et al. |
| 2006/0293682 A1 | 12/2006 | Justin et al. |
| 2007/0233138 A1 | 10/2007 | Figueroa et al. |
| 2007/0288029 A1 | 12/2007 | Justin |
| 2008/0188855 A1 | 8/2008 | Brown et al. |
| 2008/0188942 A1 | 8/2008 | Brown et al. |
| 2008/0234683 A1 | 9/2008 | May |

FOREIGN PATENT DOCUMENTS

| | | |
|---|---|---|
| EP | 0502737 B1 | 11/1995 |
| EP | 1550419 A2 | 7/2005 |
| EP | 1550419 A3 | 7/2005 |
| FR | 2682589 A1 | 4/1993 |
| WO | WO91/06260 A1 | 5/1991 |
| WO | WO98/04202 A1 | 2/1998 |
| WO | WO2004/002332 A1 | 1/2004 |
| WO | WO2005/069809 A2 | 8/2005 |
| WO | WO2005/069809 A3 | 8/2005 |

* cited by examiner

PATELLO-FEMORAL MILLING SYSTEM

CROSS-REFERENCE TO RELATED APPLICATION

This application claims the benefit of U.S. Provisional Patent Application Ser. No. 61/098,352, filed Sep. 19, 2008, the disclosure of which is expressly incorporated herein by reference in its entirety.

BACKGROUND

1. Field of the Invention

The present invention relates to a guided orthopedic milling system. More particularly, the present invention relates to a guided orthopedic milling system for preparing a surface of an anatomical structure to receive an orthopedic prosthesis, and to a method for using the same.

2. Description of the Related Art

During flexion and extension of the knee, the patella glides across the front of the femur in a shallow groove, referred to as the femoral trochlea. If the femoral trochlea becomes damaged due to disease or trauma, for example, the patella may articulate improperly across the femoral trochlea and may dislocate from the femur. Disease and trauma affecting the patello-femoral joint of a knee are commonly treated by surgically replacing the femoral trochlea with a femoral trochlea prosthesis, according to a procedure known as a patello-femoral joint replacement. Preparing the femur to receive the femoral trochlea prosthesis requires a highly accurate and repeatable technique.

SUMMARY

The present invention provides a guided orthopedic milling system for preparing a surface of an anatomical structure to receive an orthopedic prosthesis, and a method for using the same. The orthopedic system includes a surgical instrument and a guide. The guide includes at least one track that is sized to receive the surgical instrument while preparing the surface of the anatomical structure.

According to an embodiment of the present invention, an orthopedic system is provided for resecting a bone. The orthopedic system includes a surgical instrument and a guide. The guide includes an anterior portion and a distal portion that is at least partially elevated relative to the anterior portion. The distal portion includes a top surface, a bottom surface and at least one track extending from the top surface to the bottom surface that is sized to receive the surgical instrument.

In one aspect, the guide may include a bridge portion that extends upwardly from the anterior portion to connect the anterior portion to the distal portion. The anterior portion of the guide may be essentially planar. The distal portion may also be oriented at an acute angle relative to the anterior portion.

In another aspect, the orthopedic system may include at least one movable projection having a retracted position with an end of the at least one movable projection being a first distance from the distal portion and at least one extended position with the end of the at least one movable projection being a second distance from the distal portion. The second distance is greater than the first distance.

In yet another aspect, the surgical instrument of the orthopedic system may include a milling burr, with the track being configured to cooperate with the milling burr to create a central resection portion, a lateral resection portion and a medial resection portion. The lateral resection portion and the medial resection portion each have planar surfaces that are angled with respect the central resection portion, so that the resection of the bone is substantially V-shaped.

According to another embodiment of the present invention, an orthopedic guide for resecting a bone includes a body and at least one movable projection extending through the body. The body includes a top surface, a bottom surface and at least one track extending from the top surface to the bottom surface of the body. The at least one movable projection has a referencing end, and is configured to be moved between a set position, a retracted position and an extended position. In the set position, the referencing end is spaced from the bottom surface of the body by a first distance. In the retracted position, the referencing end is spaced from the bottom surface of the body by a second distance, the second distance being less than the first distance. In the extended position, the referencing end is spaced from the bottom surface of the body by a third distance, the third distance being greater than the first distance.

In one aspect, the track defines at least one cutting tool path. The referencing end of the at least one projection is configured to disrupt the at least one cutting tool path in the set position and to avoid the at least one cutting tool path in the retracted position.

In another aspect, a difference between the first distance and the third distance corresponds to a depth of the bone that is resected.

In another aspect, the referencing end is configured to contact a non-resected surface of the bone in the set position, to avoid contact with the bone in the retracted position, and to contact a resected surface of the bone in the extended position.

In yet another aspect, the at least one movable projection comprises a medial movable projection and a lateral movable projection. Alternatively, the at least one movable projection comprises a plurality of medial movable projections and a plurality of lateral movable projections.

In still another aspect, the orthopedic guide may include a means for locking the at least one movable projection in at least one position. The position may be the set position, the retracted position and/or the extended position.

According to yet another embodiment of the present invention, a milling burr is provided that includes a body and a plurality of teeth extending from the body. The body has a distal end, the body tapering toward the distal end. The plurality of teeth project beyond the distal end of the body, and each of the plurality of teeth form an obtuse relief angle relative to a longitudinal axis of the body. Each of the plurality of teeth includes a compression face, a decompression face located opposite the compression face, and a cutting edge located between the compression face and the decompression face.

In another aspect, the distal end of the body of the milling burr may include a plurality of ramps extending proximally from the distal end. The ramps may have an angular orientation facing generally distally and away from the longitudinal axis of the body. The ramps direct material dislodged by the plurality of teeth away from the longitudinal axis.

According to another embodiment of the present invention, a method of resecting a bone is provided, the method including the following steps. A substantially flat anterior cut is made in the bone. A guide is provided, the guide including an anterior portion, a distal portion and at least one projection extending through the distal portion. The anterior portion has a substantially planar bottom surface. The distal portion is oriented angularly relative to the anterior portion. The at least one projection has a referencing end that is movable between an extended position and a retracted position, the referencing end being further from the distal portion in the extended position than in the retracted position. The at least one projection is positioned in a set position between the retracted position and the extended position. The guide is then positioned on the anterior cut with the bottom surface of the anterior portion on the anterior cut. The referencing end is positioned such that it is in contact with the bone. The guide is secured to the bone. The at least one projection is retracted to the retracted position. A surgical instrument is then engaged with the guide to resect at least a portion of the bone.

In another aspect, after the step of engaging a surgical instrument, the at least one projection is extended to the extended position to abut a resected surface of the bone In yet another aspect, the step of positioning the bottom surface of the anterior portion of the guide on the anterior cut includes aligning a distal slot in the distal portion of the guide with an intercondylar notch on the bone.

In still another embodiment, an orthopedic guide for resecting a bone includes a body and a support means for supporting the guide. The body includes a top surface, a bottom surface, and at least one track extending from the top surface to the bottom surface of the body. The support means is movable between a pre-resection position in which the support means supports the body on the bone before resection, and a post-resection position in which the support means supports the body on a portion of the bone exposed by resection.

In one aspect, the orthopedic guide also includes a cutting tool adapted to engage with the at least one track to define a cutting tool path. The support means is movable to a non-support position in which the support means avoids the cutting tool path.

In another aspect, the support means includes a medial movable projection and/or a lateral movable projection.

In yet another aspect a means for locking the support means in the pre-resection position and/or the post-resection position may be included.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 4:
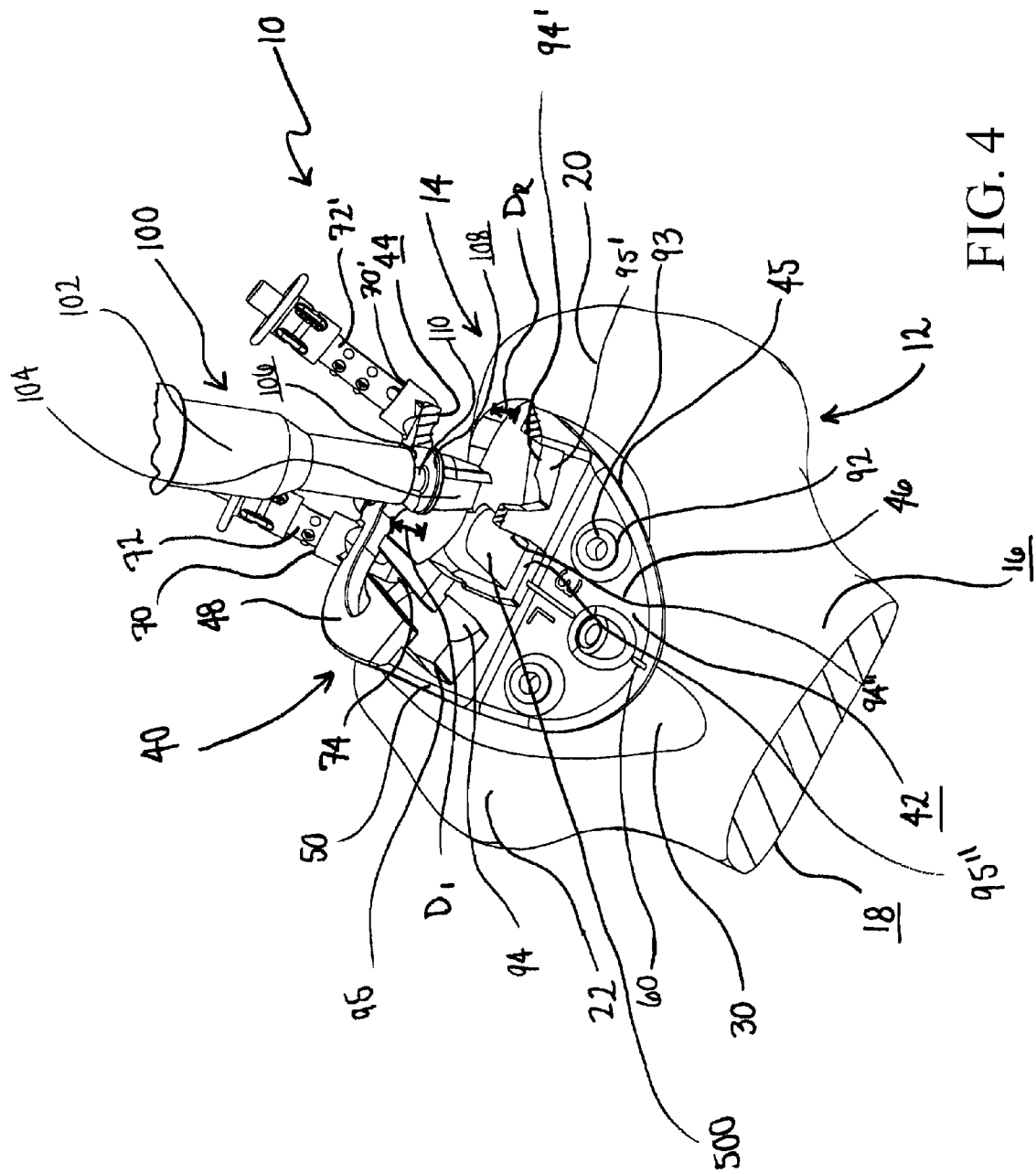
FIG. 4 is a view similar to FIG. 3 showing a surgical tool resecting a medial portion of the femur.
Figure 7:
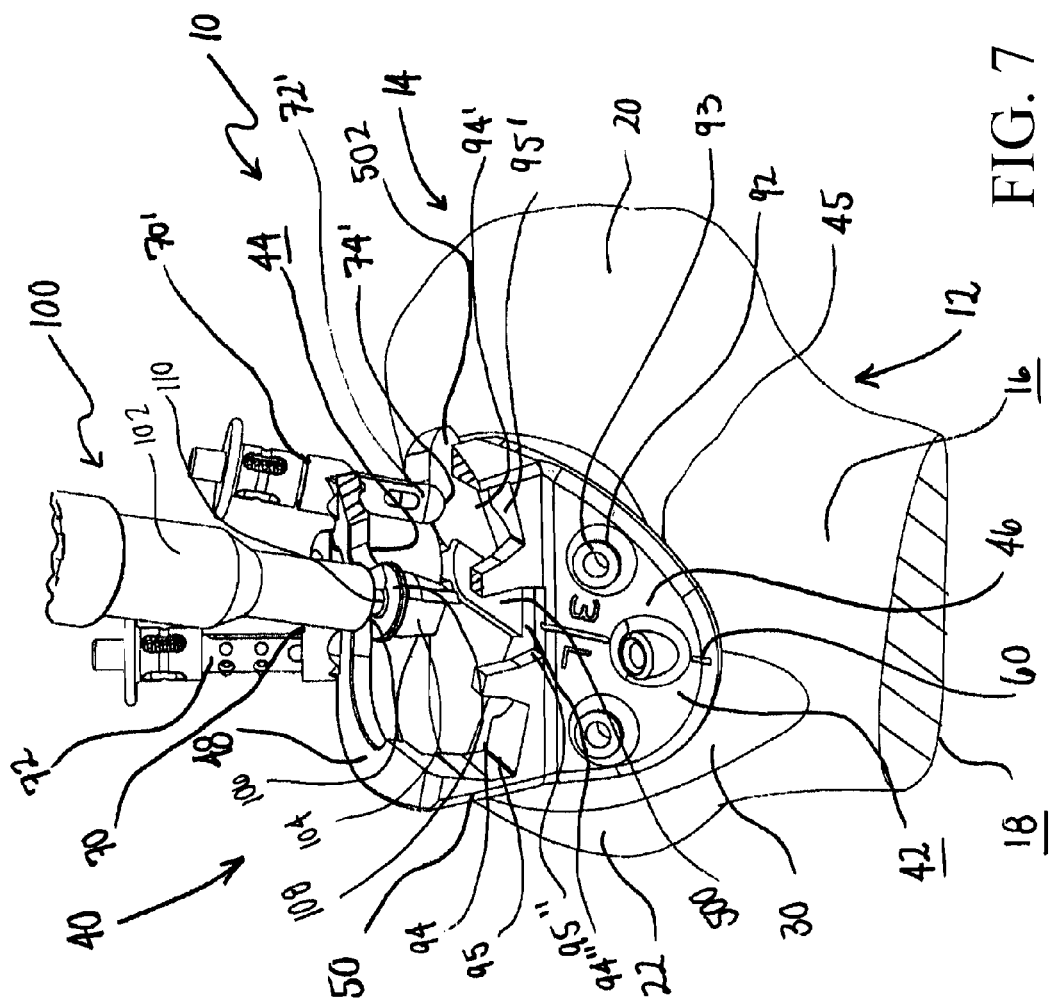
FIG. 7 is a view similar to FIG. 5 showing a surgical tool resecting a lateral portion of the femur.
Figure 9:
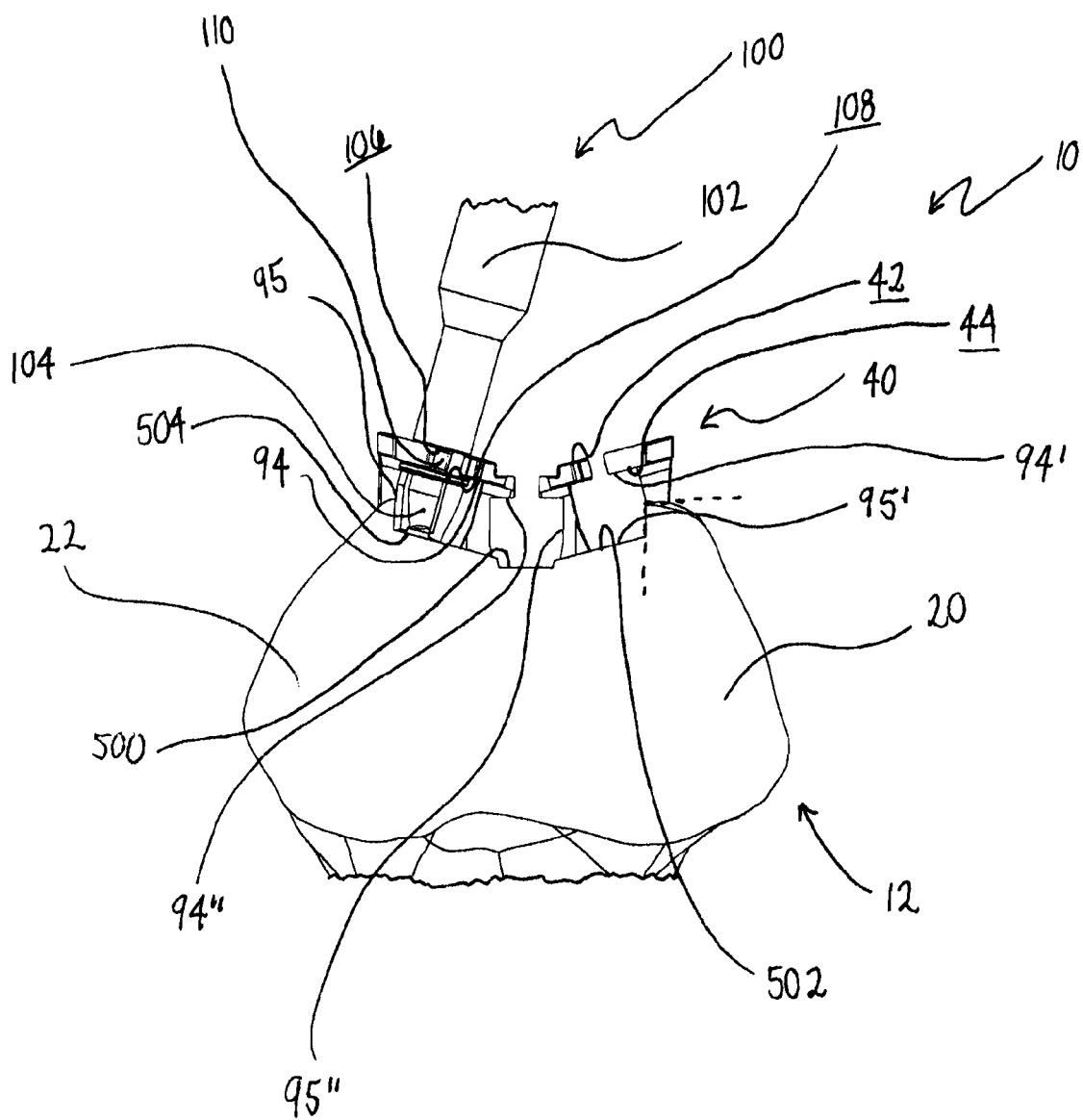
FIG. 9 is an elevational view of a surgical tool resecting a lateral portion of the femur.

Referring to FIGS. 4, 7 and 9 orthopedic system 10 is provided for preparing femur 12 to receive a femoral trochlea prosthesis (not shown). Although orthopedic system 10 is described and depicted herein as being used to prepare femur 12 to receive a femoral trochlea prosthesis, orthopedic system 10 may be used to prepare other anatomical structures to receive a prosthesis, such as the tibia, fibula, radius, ulna, clavicle, and other bones. Femur 12 includes distal end 14, anterior surface 16 and posterior surface 18. Distal end 14 of femur 12 includes medial condyle 20, lateral condyle 22, and intercondylar notch 24 located between medial condyle 20 and lateral condyle 22. Anterior surface 16 of femur 12 includes trochlea or trochlear groove 26 located between medial condyle 20 and lateral condyle 22. During flexion and extension of the knee, a patella (not shown) glides across anterior surface 16 of femur 12 in trochlear groove 26. Although femur 12 is illustrated as a left femur, orthopedic system 10 may be used to prepare a right femur using a similar procedure as described herein.

Figure 1:
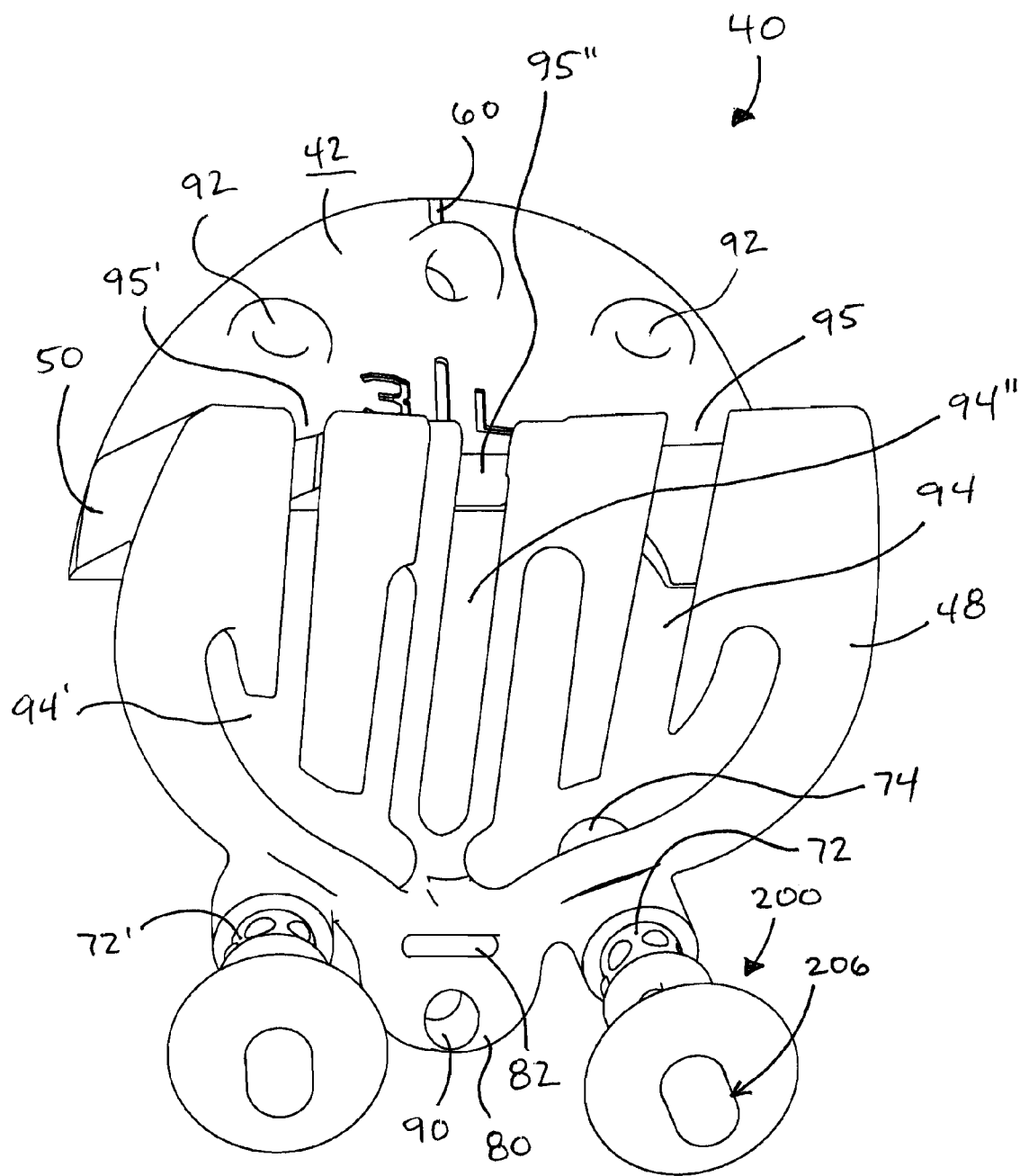
FIG. 1 is a perspective view of an orthopedic system in accordance with the present invention secured to a distal femur.
Figure 2:
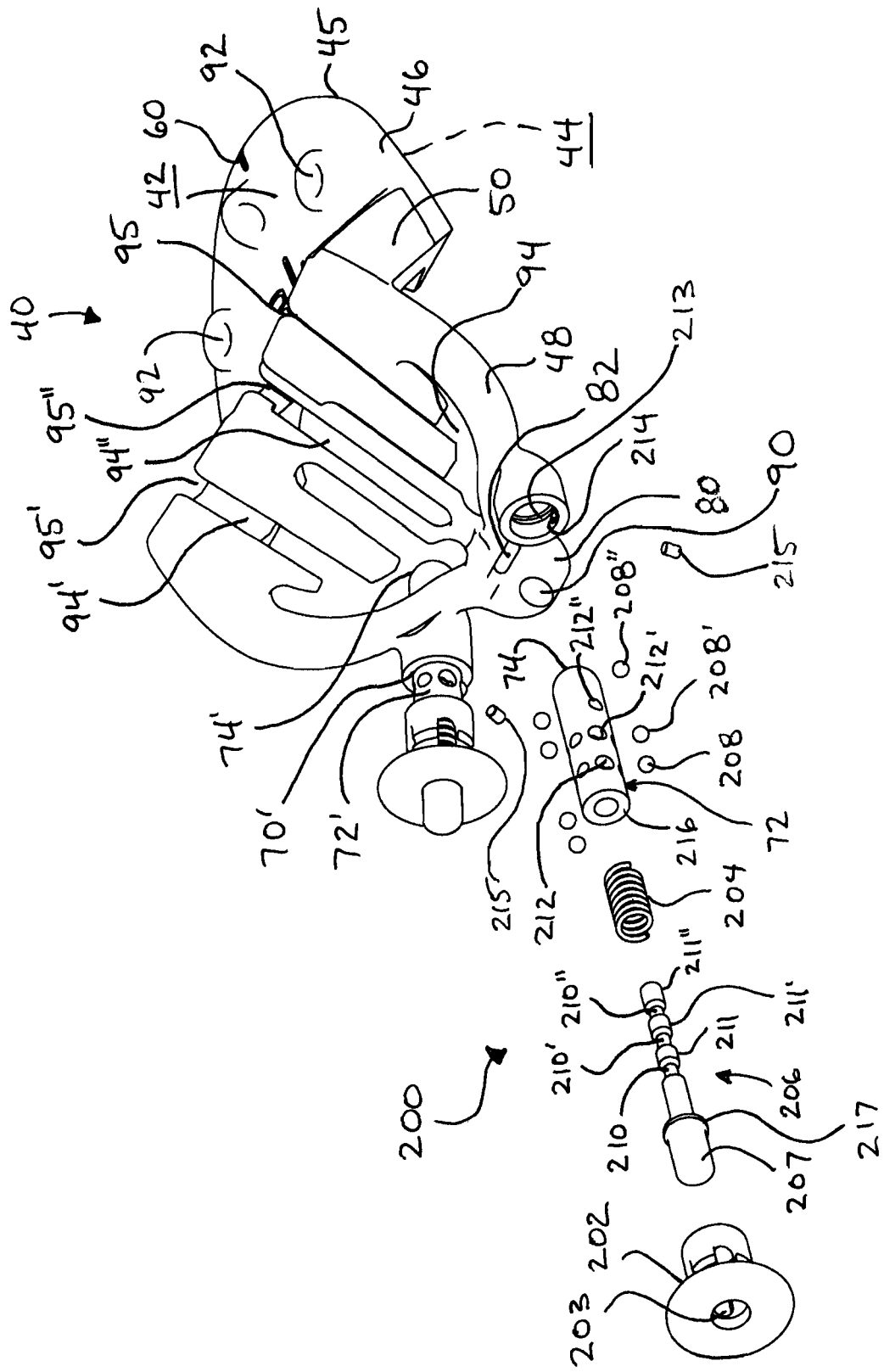
FIG. 2 is a partial exploded view of a guide in accordance with the present invention.

Orthopedic system 10 generally includes guide 40 and surgical instrument 100 (FIG. 4). Referring to FIGS. 1 and 2, guide 40 includes top surface 42, bottom surface 44, and outer periphery 45 that extends between top surface 42 and bottom surface 44. Guide 40 also includes anterior portion 46, distal portion 48, and bridge portion 50 that connects anterior portion 46 and distal portion 48. As shown in FIG. 2, bridge portion 50 extends upward from anterior portion 46 of guide 40 and distal portion 48 of guide 40 is oriented angularly relative to anterior portion 46 of guide 40. For example, distal portion 48 of guide 40 may be oriented approximately 20 degrees, 30 degrees, 40 degrees, 50 degrees, 60 degrees, or 70 degrees, relative to anterior portion 46 of guide 40. Also, as shown in FIG. 2, distal portion 48 of guide 40 may be at least partially elevated above anterior portion 46 of guide 40. For example, near bridge portion 50, distal portion 48 of guide 40 may be elevated above anterior portion 46 of guide 40.

Guide 40 also includes at least one bore for receiving a movable projection in the form of an adjustable foot. Specifically, distal portion 48 of guide 40 includes at least one bore for receiving an adjustable foot. In the illustrative embodiment of FIG. 2, distal portion 48 of guide 40 includes lateral bore 70 for receiving a movable projection in the form of lateral foot 72 and medial bore 70' for receiving a movable projection in the form of medial foot 72'. Lateral foot 72 and medial foot 72' are substantially identical, so descriptions of lateral bore 70 and lateral foot 72 may be applied to medial bore 70' and medial foot 72', and vice versa. As used herein, the terms "adjustable foot" and "foot" refer to a movable projection.

Lateral bore 70 extends through guide 40. Specifically, lateral bore 70 extends transversely through guide 40 from top surface 42 to bottom surface 44 of guide 40. According to an exemplary embodiment of the present invention, lateral bore 70 may extend at an angle through distal portion 48 of guide 40 such that lateral foot 72 received therein projects beneath bottom surface 44 of guide 40, as described in more detail below.

Lateral foot 72 includes referencing end 74. According to an exemplary embodiment of the present invention, referencing end 74 is at least partially rounded and/or has smooth edges such that referencing end 74 can be rested against cartilage or soft tissue without damaging or puncturing the cartilage.

The position of lateral foot 72 and medial foot 72' relative to guide 40 may be adjusted. According to an exemplary embodiment of the present invention, lateral foot 72 and medial foot 72' may be moved between at least a middle or set position, a retracted position, and an extended position, relative to guide 40. Also, lateral foot 72 and medial foot 72' may be selectively locked in the various positions.

Figure 3:
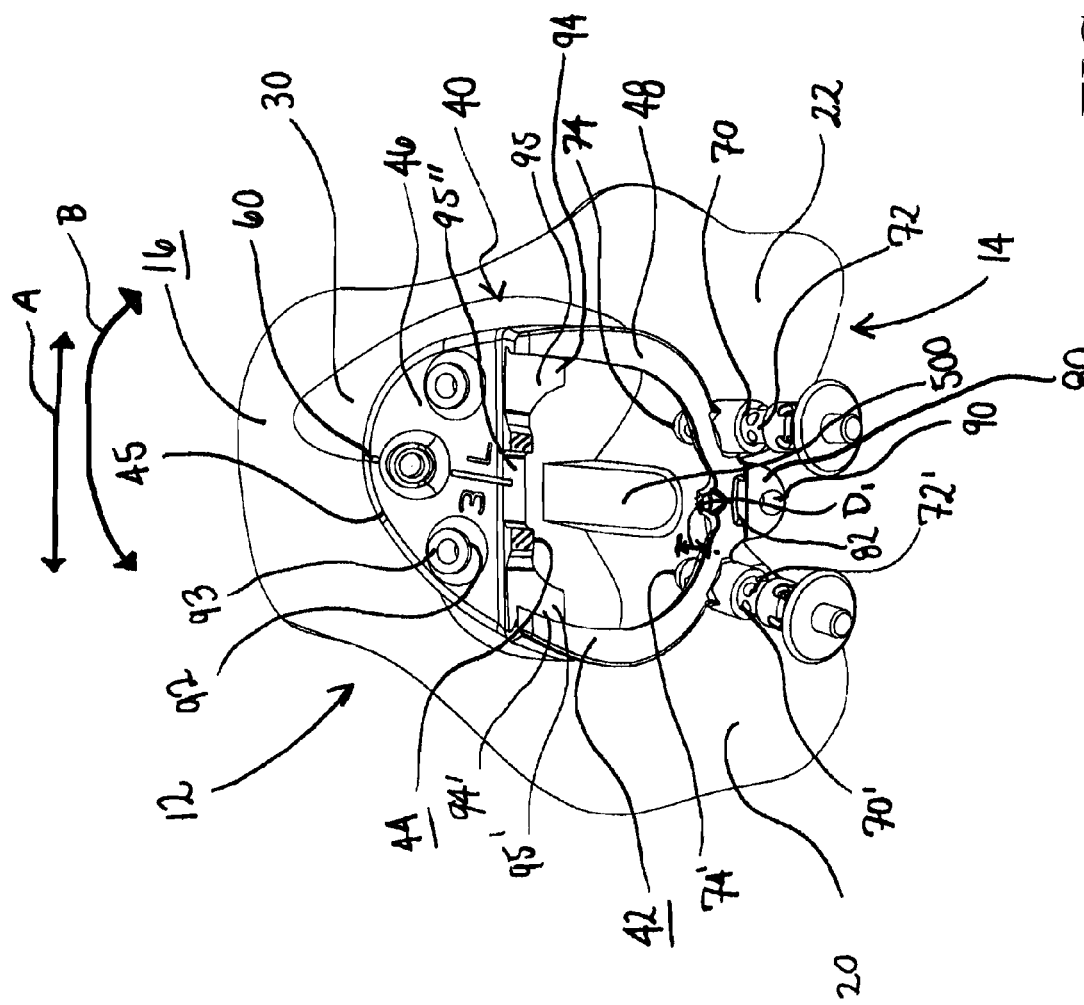
FIG. 3 is a partial cut away view of the orthopedic system of FIG. 1 showing a resected central portion of the femur.
Figure 5:
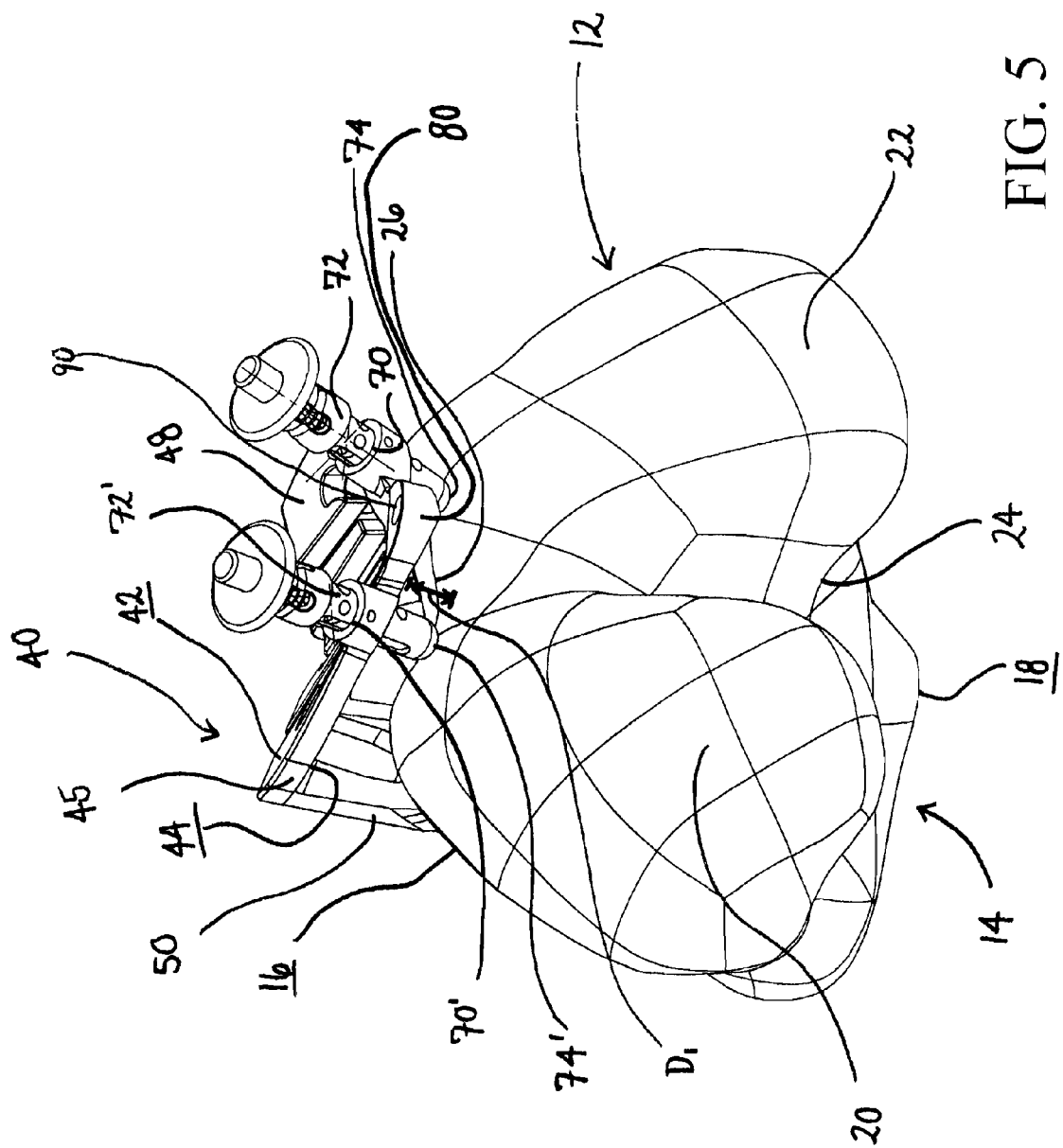
FIG. 5 is a perspective view of the orthopedic system shown in FIG. 1, illustrating the system mounted to a femur.

Both lateral foot 72 and medial foot 72' are illustrated in the middle position in FIGS. 3 and 5. In this middle position, referencing ends 74, 74', extend a first distance $D_1$ from bottom surface 44 of distal portion 48 of guide 40.

Lateral foot 72 is illustrated in the retracted position in FIG. 7, and medial foot 72' is illustrated in the retracted position in FIG. 4. In this retracted position, lateral foot 72 and medial foot 72' are raised within lateral bore 70 and medial bore 70', respectively. Referencing ends 74, 74', extend a second distance $D_2$ (not labeled) from bottom surface 44 of distal portion 48 of guide 40, the second distance $D_2$ being less than the first distance $D_1$. It is within the scope of the present invention that the second distance $D_2$ may be less than or equal to zero, meaning that referencing ends 74, 74', could be raised level with or above bottom surface 44 of distal portion 48 of guide 40.

Figure 6:
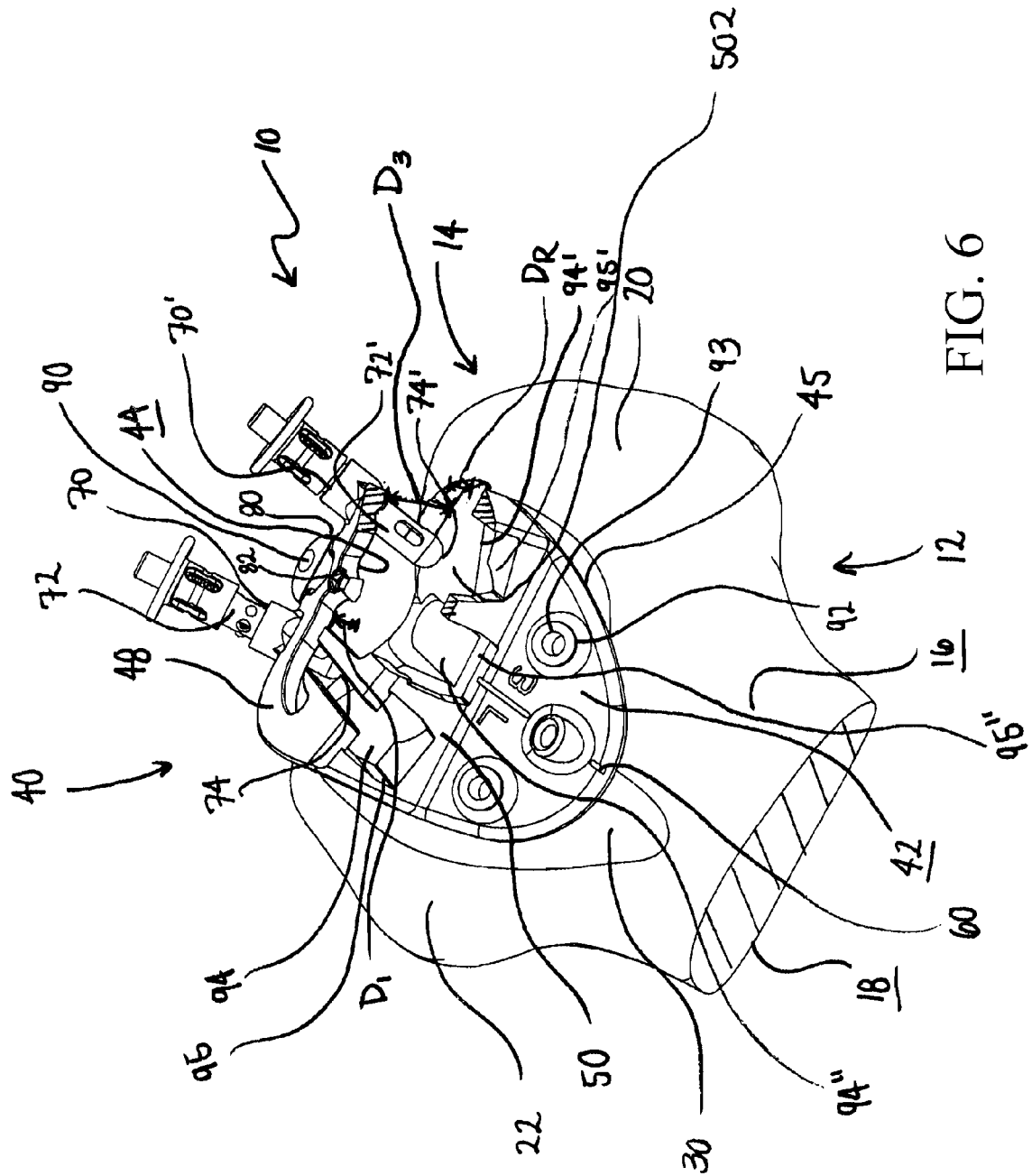
FIG. 6 is a view similar to FIG. 4 showing the resected medial portion of the femur.

Medial foot 72' is illustrated in the extended position in FIG. 6. Although not illustrated, it is also within the scope of the present invention that lateral foot 72 may be secured in the extended position. In this extended position, medial foot 72' is lowered within medial bore 70'. Referencing end 74' of medial foot 72' extends a third distance $D_3$ from bottom surface 44 of distal portion 48 of guide 40, the third distance $D_3$ being greater than the first distance $D_1$ and the second distance $D_2$.

For purposes of the present discussion, first distance $D_1$, second distance $D_2$, and third distance $D_3$, are measured perpendicularly from bottom surface 44 of distal portion 48 of guide 40. As mentioned above, the feet 72, 72', may extend at an angle relative to guide 40. Thus, the actual length of each foot 72, 72', projecting beyond bottom surface 44 of guide 40 may be greater than first distance $D_1$, second distance $D_2$, and third distance $D_3$. For example, as shown in FIG. 6, the length of medial foot 72' projecting beyond bottom surface 44 of guide 40 in the extended position exceeds third distance $D_3$.

Lateral foot 72 and medial foot 72' may include a position marker (not shown), such as a colored and/or inscribed line. When lateral foot 72, for example, is secured in the middle position, the marker may be hidden from view by lateral bore 70. When lateral foot 72 is secured in the retracted position, the marker may be viewed above lateral bore 70. When lateral foot 72 is secured in the extended position, the marker may be viewed beneath lateral bore 70. In addition to the distance between referencing end 74 and guide 40, the position marker may serve as a visual indicator of the current position of lateral foot 72.

An exemplary mechanism for adjusting the position of the feet 72, 72' relative to guide 40 is illustrated in FIG. 2 with respect to lateral foot 72. Adjustment mechanism 200 includes head piece 202, spring 204, and shaft 206 which, when assembled, are coupled to lateral foot 72. Shaft 206 includes button portion 207 and annular grooves 210, 210', 210", separated by annular ridges 211, 211', and 211". Lateral foot 72 also includes pegs or balls 208, 208', 208", and apertures 212, 212', 212". Balls 208, 208', 208", are received within apertures 212, 212', 212", respectively. Apertures 212, 212', 212" have a diameter at the outer face of lateral foot 72 that is less than the diameter of balls 208, 208', 208" to prevent balls 208, 208', 208" from passing entirely through 212, 212', 212". However, balls 208, 208', 208" pass through apertures 212, 212', 212" sufficiently far to provide locking functionality, as discussed below.

Lateral bore 70 includes at least one annular cut-out portion or rim 213. When button portion 207 is not pressed, spring 204 urges button portion 207 upward through aperture 203 in head piece 202 to a raised position. In the raised position, annular ridges 211, 211', 211" of shaft 206 align with apertures 212, 212', 212" in lateral foot 72, thereby forcing balls 208, 208', 208" to project outward from apertures 212, 212', 212". Depending on the position of lateral foot 72 in lateral bore 70, at least one of balls 208, 208', 208", projecting from lateral foot 72 may be received within annular rim 213 of lateral bore 70, causing balls thereby locking lateral foot 72 in place. Since ridges 211, 211', 211" are positioned along shaft 206 to urge balls 208, 208', 208" outward when the button portion 207 is not pressed, adjustment mechanism 200 functions to retain lateral foot 72 in a locked position unless and until button portion 207 is pressed.

On the other hand, when button portion 207 is pressed sufficiently hard to overcome the force of spring 204, spring 204 compresses and shaft 206 moves downward within the inner bore of lateral foot 72 until annular grooves 210, 210', 210" of shaft 206 align with apertures 212, 212', 212", thereby allowing balls 208, 208', 208" to retract into annular grooves 210, 210', 210" of shaft 206. The balls 208, 208', 208" that was once locked within annular rim 213 of lateral bore 70 are released, thereby permitting translation of lateral foot 72 between extended, middle and retracted positions. While an exemplary adjustment mechanism has been described herein, other known mechanisms for adjusting the position of the feet relative to guide 40 may be utilized within the scope of the present invention.

Optionally, lateral bore 70 may include at least one window 214 with a retaining element or boss 215 received therein. Boss 215 cooperates with a longitudinal groove (not shown) in the surface of lateral foot 72 to prevent complete removal of retention mechanism 200. On assembly, lateral foot 72 is inserted into lateral bore 70 with rotational orientation that aligns the longitudinal groove with window 214. Boss 215, once inserted through window 214, protrudes in to the longitudinal groove. The longitudinal groove does not extend to the end of lateral foot 72, which is to say it stops short of referencing end 74. Thus, when adjustment mechanism 200 is pulled to a point beyond the retracted position, retaining element or boss 215 impinges upon the end of the longitudinal groove and prevents any further motion that would result in removal of retention mechanism 200. Cooperation between boss 215 and window 214 may also limit downward motion, i.e., motion in the direction of the extended position, in a similar manner.

When assembled, head piece 203 attaches to lateral foot 72, such as by press-fit, welding, mechanical fastening or the like. When so attached, head piece holds spring 204 in compression between an annular end surface 216 of lateral foot 72 and a shoulder 217 of shaft 206. Aperture 203 allows button portion 207 to pass therethrough, while preventing shoulder holding shoulder 217 against spring 204.

In operation, to accommodate orthopedic system 10, a surgeon first accesses distal end 14 of femur 12, such as using a minimally invasive surgical procedure, and moves the patella (not shown). Then, the surgeon makes anterior cut 30 in anterior surface 16 of femur 12, as shown in FIG. 3. An exemplary anterior cut 30 is substantially flat and extends medially-laterally across anterior surface 16 of femur 12 beneath trochlear groove 26 (FIG. 5). Anterior cut 30 may be made utilizing a suitable cut guide and an oscillating saw, for example.

Next, a suitable guide 40 is selected from a set. The set may include guides designed for use with a right leg, guides designed for use with a left leg, and guides of various sizes and configurations. In the illustrative embodiment of FIG. 3, guide 40 includes a label "3L" indicating that guide 40 is a size 3 device and is designed for use with a left leg. According to an exemplary embodiment of the present invention, outer periphery 45 of guide 40 may correspond to the size and shape of a corresponding femoral trochlea prosthesis (not shown) to facilitate sizing and positioning of guide 40 and the prosthesis.

Then, anterior portion 46 of the selected guide 40 is positioned against anterior surface 16 of femur 12, as shown in FIG. 3. Specifically, bottom surface 44 of anterior portion 46 of guide 40 is rested against anterior cut 30 in anterior surface 16 of femur 12. Bottom surface 44 of anterior portion 46 of guide 40 may be essentially planar to rest against a correspondingly flat anterior cut 30. According to an exemplary embodiment of the present invention, anterior portion 46 of guide 40 may be slightly smaller than anterior cut 30, but anterior portion 46 of guide 40 should not overhang anterior cut 30. As mentioned above, outer periphery 45 of guide 40 may be used to visually determine whether guide 40 will correspond to an appropriately sized femoral trochlea prosthesis (not shown). If anterior portion 46 of guide 40 does overhang anterior cut 30, a smaller guide 40 may be chosen from the set provided. Similarly, if anterior portion 46 of guide 40 is significantly smaller than anterior cut 30, a larger guide 40 may be chosen from the set provided.

The position and alignment of guide 40 relative to femur 12 may be adjusted while anterior portion 46 of guide 40 is resting flush against anterior cut 30 in femur 12. As shown in FIG. 3, guide 40 may be moved medially-laterally across femur 12 in a direction indicated by arrow A. Guide 40 may include central reference marker 60 to facilitate medial-lateral positioning of guide 40. For example, central reference marker 60 may indicate the track of the femoral trochlea prosthesis (not shown) to be implanted so that a surgeon can visualize the proper medial-lateral position of guide 40. Also, as shown in FIG. 3, guide 40 may be angled or rotated with respect to femur 12 in a direction indicated by arrow B, such that bottom surface 44 of anterior portion 46 of guide 40 remains in substantially planar contact with the flat anterior cut 30. The angular alignment between guide 40 and femur 12 may be adjusted to mimic the natural Q-angle of the knee, or the angle formed between the longitudinal axis of femur 12 and an axis of the patellar tendon (not shown). The natural Q-angle of the knee varies from patient to patient. For example, the natural Q-angle of men is typically less than 15 degrees, while the natural Q-angle in women is typically less than 20 degrees. Therefore, guide 40 may be adjusted relative to femur 12 in the direction indicated by arrow B to achieve a varus alignment, in which distal portion 48 of guide 40 deviates medially with respect to femur 12 (toward medial condyle 20), or a valgus alignment, in which distal portion 48 of guide 40 deviates laterally with respect to femur 12 (toward lateral condyle 22). Central reference marker 60 described above may also facilitate varus-valgus positioning of guide 40.

After anterior portion 46 of the selected guide 40 is aligned with anterior surface 16 of femur 12, distal portion 48 of guide 40 is aligned with distal end 14 of femur 12. According to an exemplary embodiment of the present invention, distal positioning of guide 40 involves locking both lateral foot 72 and medial foot 72' in the middle position, such as by using adjustment mechanism 200 (described above), and placing referencing ends 74, 74' in contact with distal end 14 of femur 12, as shown in FIG. 5. The points of contact between femur 12 and referencing ends 74, 74' represent areas in which a distal edge of the inlayed femoral trochlea prosthesis (not shown) will transition into the surrounding cartilage and/or bone. If the surgeon determines that areas of femur 12 contacted by referencing ends 74, 74' are not suitable for the distal transition of the inlayed femoral trochlea prosthesis (not shown), a different guide 40 may be selected from the set provided and the steps described above repeated.

Advantageously, the areas of femur 12 contacted by referencing ends 74, 74' will be removed during subsequent resection of femur 12. Thus, referencing ends 74, 74' will not dent or otherwise interfere with cartilage and/or soft tissue that will remain after resection.

Also advantageously, referencing ends 74, 74' indicate or mark portions of femur 12 that will be resected. According to an exemplary embodiment of the present invention, referencing ends 74, 74' are rounded or hemispherical, as shown in FIGS. 5 and 6. Thus, the resulting small point of contact between referencing ends 74, 74' and the adjacent bore or tissue can be precisely visually determined. No visual extrapolation is required between the reference points and the resected points, because the reference points and the resected points overlap.

Figure 8:
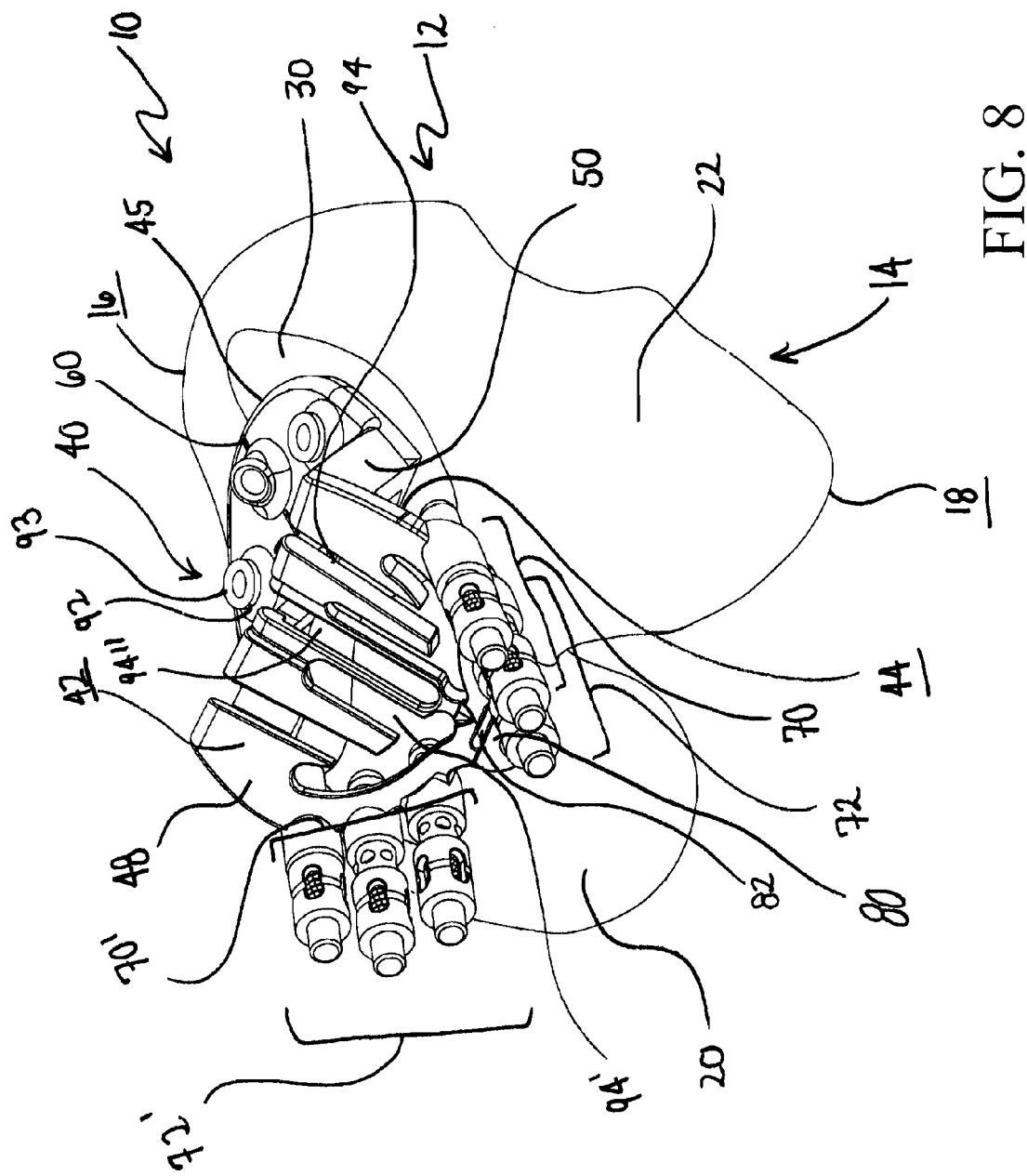
FIG. 8 is a perspective view of another orthopedic system in accordance with the present invention secured to a distal femur.

Also advantageously, guide 40 may include multiple lateral bores 70 and multiple medial bores 70', as shown in FIG. 8. Various lateral feet 72 and medial feet 72' may be received therein to accommodate different femoral trochlea prostheses (not shown). For example, lateral foot 72 and medial foot 72' located furthest from anterior portion 46 of guide 40 may correspond to a male prosthesis, lateral foot 72 and medial foot 72' located closest to anterior portion 46 of guide 40 may correspond to a youth prosthesis, and lateral foot 72 and medial foot 72' located in the middle may correspond to a female prosthesis. Also, if various lateral feet 72 and medial feet 72' are provided, the surgeon may intraoperatively select a lateral foot 72 and a corresponding medial foot 72' that represent the most suitable location for a smooth distal transition between the inlayed femoral trochlea prosthesis (not shown) and the surrounding cartilage and/or bone. As an alternative to multiple bores and multiple feet, guide 40 may have a lateral slot and a medial slot (not shown) adapted to receive a single lateral foot and a single medial foot, respectively. Each foot may be movable within its respective slot to multiple positions, such as to positions corresponding with the multiple lateral bores 70 and the multiple medial bores 72 discussed above.

The step of positioning guide 40 relative to distal end 14 of femur 12 may involve aligning distal portion 48 of guide 40 with intercondylar notch 24 of femur 12. As shown in FIGS. 1 and 5, guide 40 may include distal protrusion 80, for example, to facilitate visually aligning guide 40 with intercondylar notch 24 of femur 12.

The step of positioning guide 40 relative to distal end 14 of femur 12 may further involve ensuring that anterior portion 46 of guide 40 remains in contact with anterior cut 30, as shown in FIG. 3. If either referencing end 74 of lateral foot 72, referencing end 74' of medial foot 72', or anterior portion 46 of guide 40, does not rest against femur 12, guide 40 may need to be repositioned on femur 12, or a different guide 40 may need to be selected from the set provided and the steps described above repeated.

The step of positioning guide 40 relative to distal end 14 of femur 12 may still further involve ensuring that guide 40 does not extend beyond intercondylar notch 24 of femur 12, as shown in FIG. 3. For example, guide 40 may include a distal slot 82 to indicate the position of a distal tail of the femoral trochlea prosthesis (not shown) corresponding to the selected guide 40, as shown in FIGS. 2 and 3. The surgeon may look through distal slot 82, or insert an instrument through distal slot 82, to ensure proper alignment of distal slot 82 and intercondylar notch 24 indicating that the distal tail of the prosthesis, when implanted, will not extend beyond intercondylar notch 24 of femur 12. If distal slot 82 of guide 40 extends beyond intercondylar notch 24 of femur 12, a different guide 40 may be selected from the set provided and the steps described above repeated.

Once guide 40 is properly aligned with femur 12, both anteriorly and distally, guide 40 may be secured to femur 12. As shown in FIG. 3, guide 40 may be secured to femur 12 by drilling screws 93, nails, or other suitable anchors, through apertures 92 in anterior portion 46 of guide 40, for example. Optionally, for additional fixation to femur 12, aperture 90 may be provided in distal portion 48 of guide 40. Any suitable number and arrangement of apertures 90, 92, may be provided. When drilling into anterior surface 16, screw 93 should be of a length that is small enough to avoid drilling beyond posterior surface 18 of femur 12.

Advantageously, apertures 90, 92 may also facilitate referencing for subsequent surgical steps. For example, anchors may be inserted into some apertures 90, 92, and headless pins may be inserted into other apertures 90, 92. After milling, the anchors may be extracted from femur 12 to remove guide 40, while leaving the headless pins in place in femur 12. These headless pins may then serve as reference points for subsequent surgical steps. For example, a drilling guide may include apertures that receive the headless pins to ensure consistent and proper positioning of the drilling guide. Once it is properly positioned, the drilling guide may be used to drill a distal tail hole in femur 12 or holes for implanting a unicondylar prosthesis, for example.

After guide 40 is secured to femur 12, the surgeon should once again verify that guide 40 is properly aligned with femur 12. For example, the surgeon should verify that referencing end 74 of lateral foot 72 is resting against distal end 14 of femur 12 in a middle or set or pre-resection position, referencing end 74' of medial foot 72' is resting against distal end 14 of femur 12, also in a middle or set or pre-resection position, and anterior portion 46 of guide 40 is resting against anterior cut 30 of femur 12. If guide 40 is over-tightened onto femur 12, the cut may be made too deep into femur 12. Guide 40 may be over-tightened onto femur 12 if referencing ends 74, 74' are depressing or denting the surrounding cartilage. On the other hand, if guide 40 is not adequately tightened onto femur 12, the cut may be made too shallow into femur 12. Guide 40 may not be adequately tightened onto femur 12 if gaps or spaces are present between femur 12 and referencing ends 74, 74'. According to an exemplary embodiment of the present invention, referencing ends 74, 74' should just contact the surface of femur 12 in their respective set positions before resection, resting flush against the bone and/or surrounding cartilage.

With guide 40 secured to femur 12, distal end 14 of femur 12 may be resected using surgical instrument 100, as shown in FIG. 4. Surgical instrument 100 may generally include handpiece 102, burr 104, top abutment surface 106, bottom abutment surface 108, tapered receiving surface 110 located between top abutment surface 106 and bottom abutment surface 108, and rotating shaft 103 (FIG. 10) that extends through handpiece 102. Burr 104 is coupled to rotating shaft 103 for rotation therewith, as shown in FIG. 9. Burr 104 is configured to cut bone when it is placed against bone and rotated via the rotating shaft. According to an exemplary embodiment of the present invention, burr 104 is rotated at approximately 30,000 rpm, which has been shown to provide an optimum balance between controllability of surgical instrument 100 and bone removal. In comparison, if burr 104 is rotated at a higher speed, such as 100,000 rpm, controllability may improve, but more heat will be generated and less aggressive cutting teeth will be necessary.

An exemplary surgical instrument 100 is described in U.S. patent application Ser. No. 11/687,763, entitled HANDPIECE CALIBRATION DEVICE, filed on Mar. 19, 2007 and assigned to the assignee of the present application, the disclosure of which is hereby expressly incorporated herein by reference in its entirety. This exemplary surgical instrument 100 includes a defined distance between burr 104 and bottom abutment surface 108 to control the depth of insertion of burr 104 into femur 12, as described in more detail below.

Figure 10:
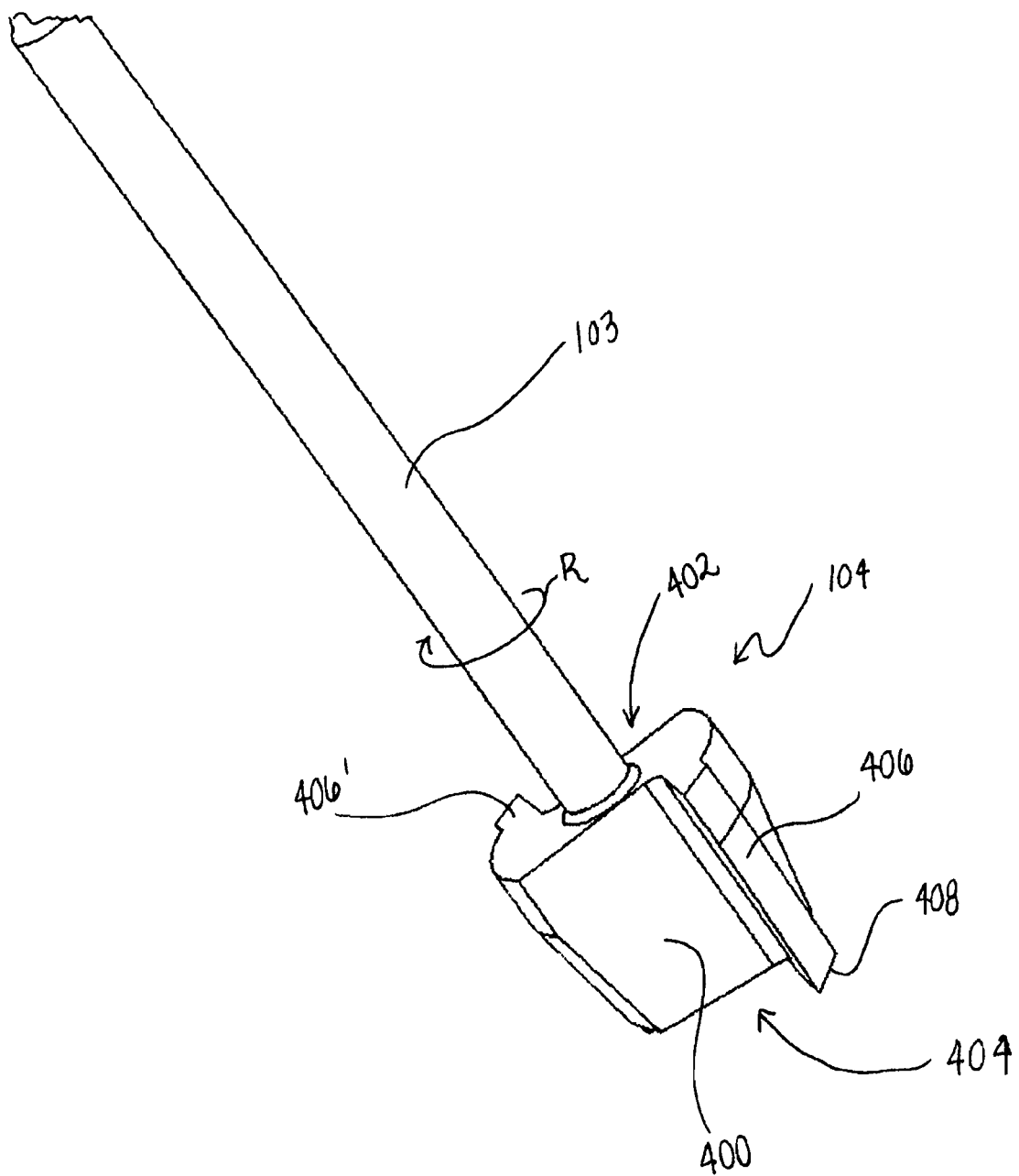
FIG. 10 is a perspective view of a burr in accordance with the present invention.
Figure 11:
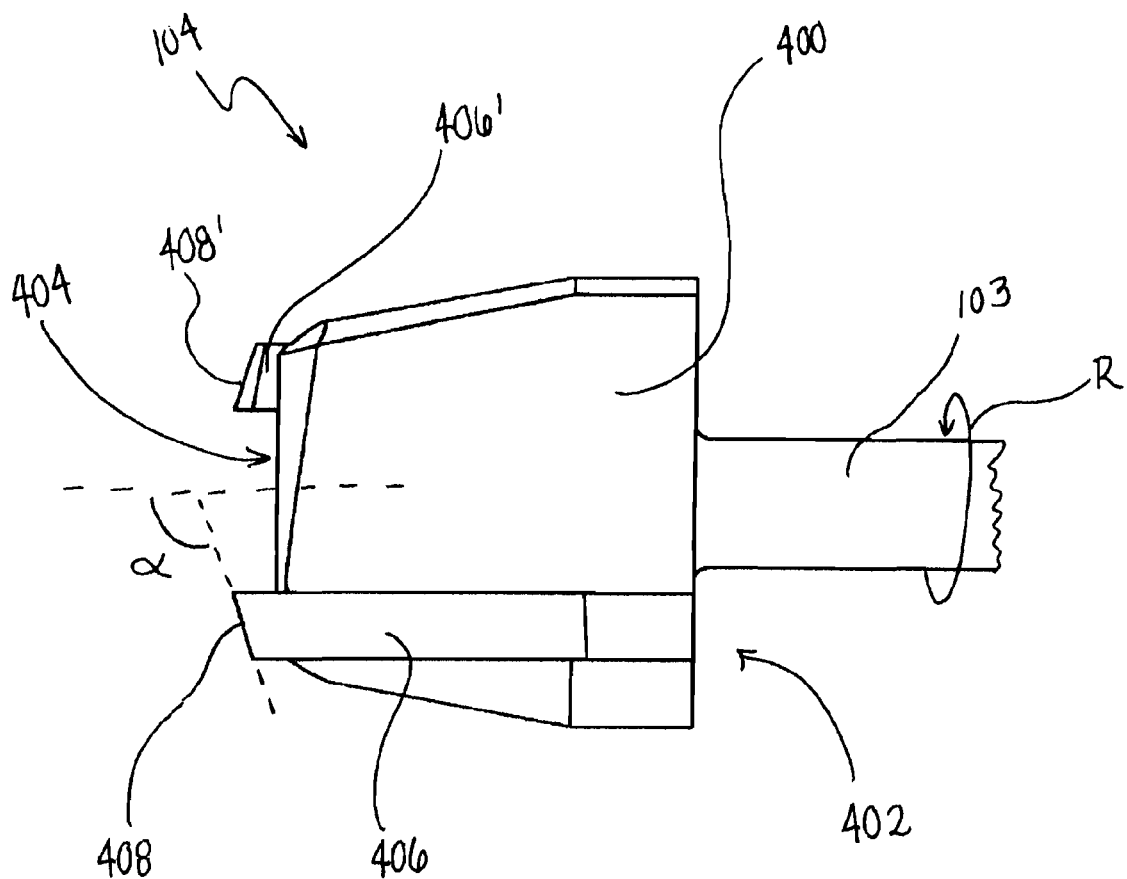
FIG. 11 is a side elevational view of the burr of FIG. 9.
Figure 12:
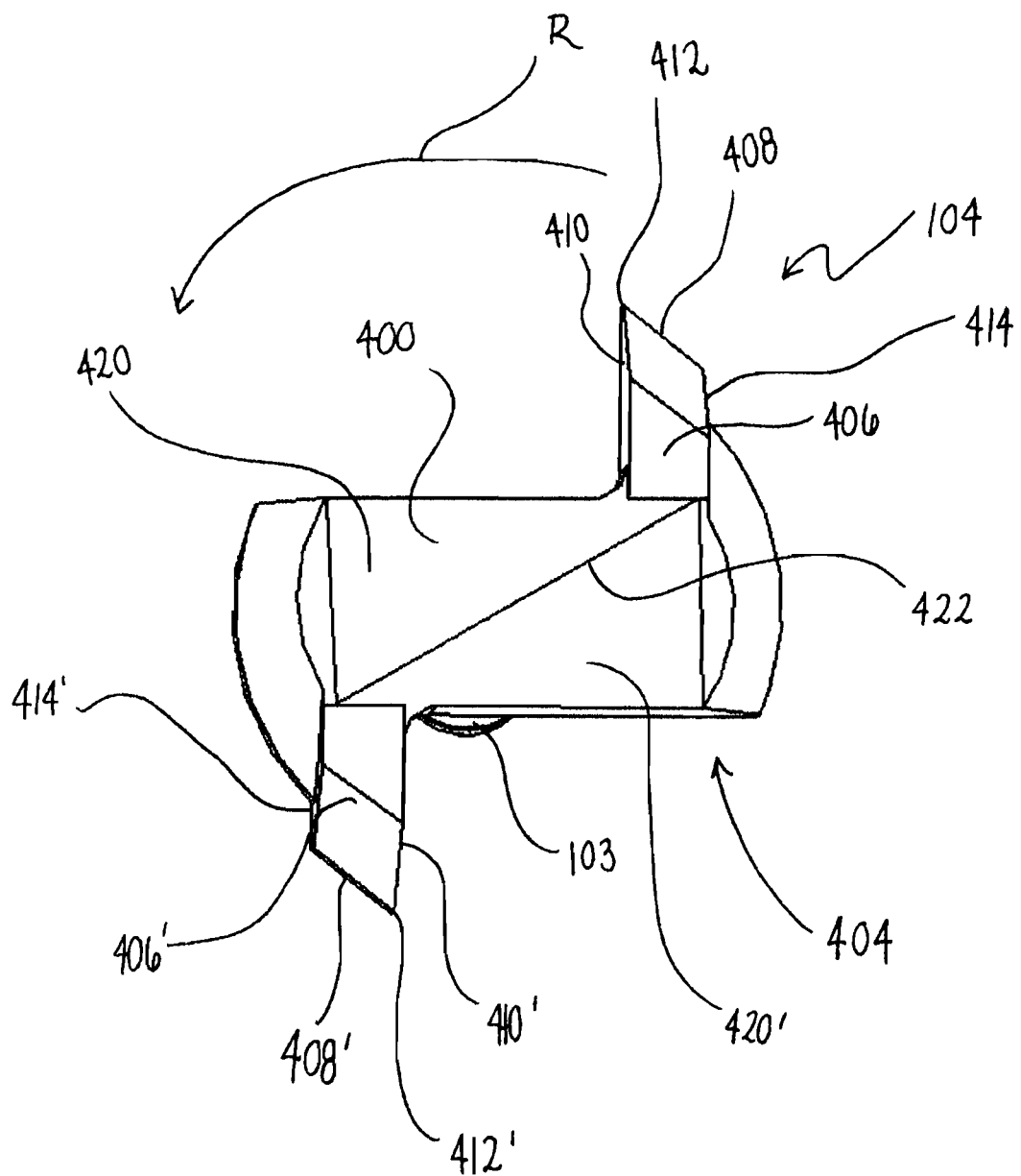
FIG. 12 is distal plan view of the burr of FIG. 9.

An exemplary burr 104 is illustrated in FIGS. 10-12. Burr 104 may be constructed of stainless steel, such as 455 SST or 465 SST, or another suitable material, for example. As shown in FIG. 10, burr 104 includes a substantially elliptical-shaped body 400 that tapers from proximal end 402 of body 400 to distal end 404 of body 400.

Burr 104 also includes two teeth 406, 406', that extend from opposite corners of body 400. As shown in FIG. 11, teeth 406, 406', may include distal ends 408, 408', that project beyond distal end 404 of body 400. Like body 400, teeth 406, 406', may taper distally. Distal ends 408, 408', of teeth 406, 406', may form an obtuse relief angle $\alpha$ relative to the longitudinal axis of rotating shaft 103. For example, relief angle $\alpha$ may equal approximately 95 degrees, 100 degrees, 105 degrees, 107 degrees, 110 degrees, 115 degrees, or more. As burr 104 is placed in contact with femur 12 and rotated in the direction indicated by arrow R, distal ends 408, 408', of teeth 406, 406', cut into the bone of femur 12. Because teeth 406, 406', project beyond distal end 404 of body 400, distal end 404 of body 400 will not rotate directly against the bone of femur 12 during milling. Minimizing contact between femur 12 and body 400 reduces the heat generated during milling.

Referring next to FIG. 12, each tooth 406, 406' includes a compression face 410, 410', a cutting edge 412, 412', and a decompression face 414, 414'. As burr 104 rotates in the direction indicated by arrow R, cartilage is first contacted by compression faces 410, 410' of teeth 406, 406'. As burr 104 continues to rotate, the compressed cartilage contacts sharp cutting edges 412, 412' of teeth 406, 406', which cuts cartilage away from femur 12. As burr 104 continues to rotate, any remaining cartilage not removed by cutting edges 412, 412' of teeth 406, 406' is allowed to decompress beyond decompression faces 414, 414' of teeth 406, 406'. Because body 400 of burr 104 is set back from decompression faces 414, 414' of teeth 406, 406', the remaining cartilage may expand to a normal, decompressed state without contacting body 400 of burr 104 until contacted by the next compression face 410, 410'. Just as minimizing contact between femur 12 and body 400 reduces the heat generated during milling, minimizing contact between cartilage and body 400 also reduces the heat generated during milling.

Referring still to FIG. 12, distal end 404 of body 400 may include ramps 420, 420', that extend proximally from distal-most portion 422 of body 400. Ramps 420, 420 are generally triangular in shape and have an angular orientation facing generally distally and away from the longitudinal axis of shaft 103. As burr 104 rotates against femur 12, bone chips away from femur 12. When these chips contact ramps 420, 420', the chips are directed toward teeth 406, 406', rather than being allowed to collect near the center of distal end 404 of body 400.

Advantageously, burr 104 has been shown to effectively cut both cartilage and bone simultaneously, which eliminates the need to manually remove cartilage prior to cutting bone. For example, distal ends 408, 408' of teeth 406, 406' may cut into the bone of femur 12 (FIG. 11), while compression faces 410, 410' and cutting edges 412, 412' of teeth 406, 406' may cooperate to remove cartilage (FIG. 12).

Also advantageously, burr 104 may generate a limited quantity of heat when cutting bone. In fact, an exemplary burr 104 has been shown to generate almost no heat when cutting bone. As discussed above, the heat produced during milling has been substantially eliminated by minimizing contact between body 400 of burr 104 and adjacent anatomical structures. Irrigation, which is typically performed to lower the temperature of the bone during milling, may not be required when using burr 104. The limited heat produced may also reduce the occurrence of necrosis.

Although surgical instrument 100 is illustrated and described herein as a milling instrument, any other suitable surgical instrument may also be utilized with orthopedic system 10, such as a laser instrument, an ultrasonic instrument, an abrasive water jet instrument, a radiofrequency cautery instrument, an oscillating instrument, or a reciprocating instrument, for example. Surgical instrument 100 may be used to prepare femur 12 via any suitable process, such as morselizing bone, abrading cartilage, preparing tissue for bone cement, or removing tissue, for example.

As described above, distal portion 48 of guide 40 includes top surface 42 and bottom surface 44. Distal portion 48 of guide 40 also defines a plurality of apertures or tracks therein that extend from top surface 42 to bottom surface 44 of guide 40. In the illustrative embodiment of FIGS. 1 and 2, distal portion 48 of guide 40 includes lateral track 94, medial track 94', and central track 94". The number, size, and arrangement of the tracks may vary depending on the size of guide 40, surgical instrument 100 being used, and the desired resection of femur 12, for example.

Referring next to FIG. 9, surgical instrument 100 and guide 40 may have an interlocking engagement, similar to a tongue and groove engagement, to control the position of surgical instrument 100 relative to guide 40. As a result, the position of surgical instrument 100 relative to femur 12 may be controlled. Surgical instrument 100 may be inserted into open ends 95, 95', 95" of lateral track 94, medial track 94', and central track 94", respectively. As shown in FIGS. 1 and 7, these open ends 95, 95', 95" are located near bridge portion 50 of guide 40. Because bridge portion 50 is elevated relative to femur 12, surgical instrument 100 may be inserted into open ends 95, 95', 95" and powered on before contacting bone.

Referring still to FIG. 9, once surgical instrument 100 is received within lateral track 94, medial track 94', and/or central track 94", the movement of surgical instrument 100 relative to guide 40 is constrained by top abutment surface 106 and bottom abutment surface 108. Tapered receiving surface 110 of surgical instrument 100 may be received between the walls of guide 40 surrounding tracks 94, 94', 94", permitting surgical instrument 100 to slide along tracks 94, 94', 94". However, top abutment surface 106 of surgical instrument 100 may abut top surface 42 of guide 40 to prevent surgical instrument 100 from being pushed beyond guide 40 toward femur 12, and bottom abutment surface 108 of surgical instrument 100 may abut bottom surface 44 of guide 40 to prevent surgical instrument 100 from being pulled away from guide 40 and femur 12. Thus, the depth of insertion of burr 104 into femur 12 may be governed by the distance between top surface 42 and/or bottom surface 44 of guide 40, for example, and femur 12. The distance between top surface 42 and/or bottom surface 44 of guide 40 and femur 12 may vary across guide 40 to alter the depth of insertion of burr 104 into femur 12 at various locations across femur 12. For example, as shown in FIG. 9, distal portion 48 of guide 40 may be V-shaped to cause burr 104 to be inserted deeper into femur 12 near the center of guide 40 than near the edges of guide 40. Advantageously, the femoral trochlea prosthesis (not shown) to be implanted may have a V-shaped exterior profile, so resecting a V-shaped area of femur 12 minimizes the volume of bone resected and allows for a thinner implant.

According to an exemplary embodiment of the present invention, burr 104 of surgical instrument 100 may have a diameter that is larger than the width of tracks 94, 94', 94". Therefore, burr 104 may undercut tracks 94, 94', 94". As shown in FIG. 2, tracks 94, 94', 94" need not cover the entire surface of guide 40 to facilitate formation of a completely resected surface on femur 12, because the cuts occurring beneath guide 40 may overlap. Moreover, the spacing and arrangement of tracks on guide 40 may be altered to allow a desired milled surface to be created with a given burr or set of burrs. In the embodiment shown in FIG. 2, lateral track 94 and medial track 94' extend distally along first path sections from open ends 95 and 95', respectively. Tracks 94, 94' then extend along respective second arcuate path sections, one medially and the other laterally. Third path sections of tracks 94, 94' extend proximally from respective medial portions of the arcuate paths, such that each third path sections is substantially parallel to each first path section. Central track 94" extends distally from open end 95" along a substantially straight path. It is within the scope of the present invention that the number, arrangement and geometry of the tracks may be varied, such as to accommodate different burr sizes, alternative areas or geometries of desired resected surfaces, or the like.

According to another exemplary embodiment of the present invention, orthopedic system 10 may be provided with a tool sizing apparatus (not shown). This apparatus may engage tracks 94, 94', 94" of guide 40 and extend beneath guide 40 toward femur 12, just as surgical instrument 100 engages tracks 94, 94', 94" of guide 40 and extends beneath guide 40 toward femur 12. The apparatus may be provided in various sizes corresponding to sizes of various burrs 104. When inserted into guide 40 toward femur 12, the apparatus may be used to visually determine a desired size of burr 104. Also, the apparatus may be used to verify the depth of resection after milling.

Referring to FIG. 3, to mill a central portion of femur 12, surgical instrument 100 is inserted into open end 95" of central track 94", powered on, and then pulled distally through central track 94". The bone of femur 12 located beneath central track 94" of guide 40 (central resection portion 500) is milled away by rotating burr 104 of surgical instrument 100. As mentioned above, distal portion 48 of guide 40 may be V-shaped, such that central track 94" is located closer to femur 12 than lateral track 94 and medial track 94". Thus, central resection portion 500 may extend deeper into femur 12 than the lateral resection portion 504 and medial resection portion 502, and the lateral and medial resection portions 504, 502 each define planar surfaces that are angled with respect to central resection portion 500 and one another.

Referring next to FIG. 4, before milling a medial portion of femur 12, medial foot 72' is moved from the middle position to the retracted position, such that medial foot 72' is pulled away from femur 12 to make room for a cutting path of surgical instrument 100 in medial track 94'. To mill the medial portion of femur 12, surgical instrument 100 is inserted into open end 95' of medial track 94', powered on, pulled distally through medial track 94', moved along the arcuate path of track 94', and pulled proximally along the central portion of track 94'. The bone of femur 12 located beneath medial track 94' of guide 40 (medial resection portion 502 of FIG. 6) is milled away by rotating burr 104 of surgical instrument 100.

Referring next to FIG. 6, after milling the medial portion of femur 12, medial foot 72' is moved from the retracted position to the extended position, such that medial foot 72' is placed in contact with resected bone of femur 12. According to an exemplary embodiment of the present invention, the difference between the extended position of medial foot 72' and the middle position of medial foot 72' (third distance $D_3$ minus first distance $D_1$) corresponds to the resection depth $D_R$ of femur 12 at the point of contact between referencing end 74' of medial foot 72' and femur 12. Thus, in the extended or post-resection position, medial foot 72' abuts the resected portion of femur 12 after resection and supports guide 40 on the medial resection portion 502 of femur 12, conferring additional stability to guide 40 for any subsequent milling or cutting process (such as described below). The added stability may provide advantages for subsequent cutting, such as reduced vibration of guide 40, better accuracy in subsequent resections, and the like.

Referring next to FIG. 7, before milling a lateral portion of femur 12, lateral foot 72 is moved from the middle position to the retracted position, such that lateral foot 72 is pulled away from femur 12 to make room for a cutting path of surgical instrument 100 in lateral track 94. To mill the lateral portion of femur 12, surgical instrument 100 is inserted into open end 95 of lateral track 94, powered on, pulled distally through lateral track 94, moved along the arcuate path of track 94, and pulled proximally along the central portion of track 94. The bone of femur 12 located beneath lateral track 94 of guide 40 (lateral resection portion 504 of FIG. 9) is milled away by rotating burr 104 of surgical instrument 100.

After milling the lateral portion of femur 12, lateral foot 72 may be moved from the retracted position to the extended or post-resection position, such that lateral foot 72 is placed in contact with resected bone of femur 12. According to an exemplary embodiment of the present invention, the difference between the extended position of lateral foot 72 and the middle position of lateral foot 72 corresponds to the resection depth of femur 12 at the point of contact between referencing end 74 of lateral foot 72 and femur 12. Thus, in the extended or post-resection position, lateral foot 72 may support guide 40 after resection on the resected lateral portion of femur 12, and may provide added stability in a similar manner as described above with respect to medial foot 72'. However, it is also within the scope of the present invention that lateral foot 72 need not require an extended position, because, after milling the lateral portion of femur 12, guide 40 may be immediately removed from femur 12.

Advantageously, the step of moving feet 72, 72' into the extended position to support guide 40 simultaneously verifies whether femur 12 was properly resected. For example, if feet 72, 72' hover above the resected bone when in the extended position, the resection may be too deep, and if feet 72, 72' contact the resected bone before being fully extended, the resection may be too shallow. To correct a shallow cut, feet 72, 72' may include a scale that indicates the depth of additional bone that should be removed to properly rest feet 72, 72' against the resected bone in the extended position.

According to an exemplary embodiment of the present invention, even if guide 40 is V-shaped as shown in FIG. 9, surgical instrument 100 may produce essentially perpendicular cut edges. In other words, even if surgical instrument 100 is oriented at an angle relative to femur 12 during milling, surgical instrument 100 may produce essentially perpendicular cut edges. For example, as shown in FIG. 9, the edge of medial resection portion 502 may extend essentially perpendicular to the non-resected medial portion of femur 12. Advantageously, surgical instrument 100 may avoid undercutting the non-resected portions of femur 12, which may weaken femur 12 along the resection border. This exemplary resection may be achieved by providing burr 104 that tapers distally, for example, as discussed above.

After resecting distal end 14 of femur 12, femur 12 may be prepared to receive a femoral trochlea prosthesis (not shown). For example, peg holes (not shown) may be drilled into femur 12. Also, femur 12 may be cleaned to remove any debris left over from milling.

The femoral trochlea prosthesis (not shown) may be selected from a set that includes prostheses of various shapes and sizes, each corresponding to a different guide. According to an exemplary embodiment of the present invention, the selected femoral trochlea prosthesis may have a size and shape that is designed to fill the portion of bone that was removed from femur 12 using the selected guide 40. Specifically, the selected femoral trochlea prosthesis may have a size and shape that substantially equals the portion of bone that was removed from femur 12 using the selected guide 40 such that the prosthesis is at least partially inlayed into distal end 14 of femur 12. An inlayed prosthesis may provide a smooth transition between the prosthesis and surrounding cartilage and/or bone, which may facilitate a smooth articulation with the patella.

The femoral trochlea prosthesis (not shown) may incorporate various features and be useable in systems using the techniques and methods described in U.S. patent application Ser. No. 11/671,643, entitled FEMORAL TROCHLEA PROSTHESES, filed on Feb. 6, 2007 and assigned to the assignee of the present application, and U.S. patent application Ser. No. 11/671,645, entitled FEMORAL TROCHLEA PROSTHESES, filed on Feb. 6, 2007 and assigned to the assignee of the present application, the disclosures of which are hereby expressly incorporated herein by reference in their entireties.

The femoral trochlea prosthesis (not shown) may accommodate other implants in the knee joint, including a unicondylar femoral component. As such, guide 40 may be coupled to another cutting guide for resecting a femoral condyle during a unicondylar femoral joint replacement, for example. Guide 40 may also be coupled to a spacer to indicate proper positioning of the unicondylar femoral component.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic guide for resecting a bone, comprising:
a body that includes
an anterior portion,
a distal portion, and
a bridge portion, wherein the bridge portion extends upwardly from the anterior portion to connect the anterior portion to the distal portion, wherein the distal portion is oriented at an acute angle relative to the anterior portion, and wherein the distal portion includes
a top surface,
a bottom surface, and
at least one track extending from said top surface to said bottom surface; and
at least one movable projection extending through said body, said at least one projection having a referencing end, said at least one movable projection being configured to be moved between:
a set position, said referencing end being spaced from the bottom surface of said body by a first distance in the set position;
a retracted position, said referencing end being spaced from the bottom surface of said body by a second distance in the retracted position, the second distance being less than the first distance; and
an extended position, said referencing end being spaced from the bottom surface of said body by a third distance in the extended position, the third distance being greater than the first distance; and
wherein said track defines at least one cutting tool path, said referencing end of the at least one projection being configured to disrupt the at least one cutting tool path in the set position and to avoid the at least one cutting tool path in the retracted position.

2. The orthopedic guide of claim 1, wherein said anterior portion of said guide is essentially planar.

3. The orthopedic guide of claim 1, wherein a difference between the first distance and the third distance corresponds to a depth of the bone that is resected.

4. The orthopedic guide of claim 1, wherein said referencing end is configured to contact a non-resected surface of the bone in the set position, to avoid contact with the bone in the retracted position, and to contact a resected surface of the bone in the extended position.

5. The orthopedic guide of claim 1, wherein said at least one movable projection comprises a medial movable projection and a lateral movable projection.

6. The orthopedic guide of claim 1, wherein said at least one movable projection comprises a plurality of medial movable projections and a plurality of lateral movable projections.

7. The orthopedic guide of claim 1, comprising a means for locking said at least one movable projection in at least one position, the position being one of said set position, said retracted position and said extended position.

8. The orthopedic guide of claim 1, wherein the at least one movable projection extends through the distal portion and the anterior portion defines at least one aperture configured for accepting a bone anchor, the at least one aperture extending through the anterior portion.

9. An orthopedic guide for resecting a bone, comprising:
a body comprising:
a top surface;
a bottom surface; and
at least one track extending from said top surface to said bottom surface; and
a movable projection for supporting the guide, said movable projection being movable between a pre-resection position in which said movable projection supports said body on the bone before resection and a post-resection position in which said movable projection supports said body on a portion of the bone exposed by resection, wherein the movable projection is configured to contact tissue of a patient and where the movable projection includes a referencing end configured to prevent damaging or puncturing cartilage, and wherein said track defines at least one cutting tool path, said movable projection being configured to move to a non-support position in which said referencing end avoids the cutting tool path and a support position in which said referencing end disrupts the at least one cutting tool path.

10. The orthopedic guide of claim 9, further comprising a cutting tool adapted to engage with said at least one track to define a cutting tool path.

11. The orthopedic guide of claim 9, wherein said movable projection comprises at least one of a medial movable projection and a lateral movable projection.

12. The orthopedic guide of claim 9, comprising a means for locking said movable projection in at least one of the pre-resection position and the post-resection position.

* * * * *